(12) United States Patent
Boldt

(10) Patent No.: US 12,356,149 B2
(45) Date of Patent: Jul. 8, 2025

(54) SYSTEM COMPRISING A COMPUTER PROGRAM, HEARING DEVICE, AND STRESS EVALUATION DEVICE

(71) Applicant: GN Hearing A/S, Ballerup (DK)

(72) Inventor: Jesper Bünsow Boldt, Måløv (DK)

(73) Assignee: GN HEARING A/S, Ballerup (DK)

( * ) Notice: Subject to any disclaimer, the term of this patent is extended or adjusted under 35 U.S.C. 154(b) by 389 days.

(21) Appl. No.: 17/738,618

(22) Filed: May 6, 2022

(65) Prior Publication Data
US 2022/0295192 A1     Sep. 15, 2022

Related U.S. Application Data

(63) Continuation of application No. PCT/EP2020/084812, filed on Dec. 7, 2020.

(30) Foreign Application Priority Data

Dec. 20, 2019  (EP) .............................. 192118516.3

(51) Int. Cl.
*H04R 25/00*  (2006.01)
*G10L 25/63*  (2013.01)

(52) U.S. Cl.
CPC ............ *H04R 25/505* (2013.01); *G10L 25/63* (2013.01); *H04R 25/558* (2013.01)

(58) Field of Classification Search
CPC .... H04R 25/505; H04R 25/558; H04R 25/70; H04R 2225/81; H04R 2225/39;
(Continued)

(56) References Cited

U.S. PATENT DOCUMENTS

2007/0071262 A1* 3/2007 Rass ...................... H04R 25/70
                                                                                       381/309
2014/0369537 A1    12/2014 Pontoppidan et al.
(Continued)

FOREIGN PATENT DOCUMENTS

| CN | 101783998 | 7/2010 |
| CN | 103239236 | 8/2013 |

(Continued)

OTHER PUBLICATIONS

PCT International Search Report and Written Opinion for International Appln. No. PCT/EP2020/084812 dated Feb. 19, 2021.
(Continued)

*Primary Examiner* — Angelica M McKinney
(74) *Attorney, Agent, or Firm* — Vista IP Law Group, LLP

(57) ABSTRACT

A computing device includes: an input configured to be coupled to, or carried by, a user of a hearing device, the hearing device configured to receive sound from an environment defined by an acoustic scene; one or more memory units; and one or more processing units; wherein the one or more sensors are configured to measure a stress parameter related to stress of the user, the stress parameter being related to the acoustic scene; wherein the computing device is configured to obtain the measured stress parameter; and wherein the one or more processing units of the computing device comprise a program configured to determine an indication of stress of the user based on at least the stress parameter.

35 Claims, 8 Drawing Sheets

(58) Field of Classification Search
CPC ...... H04R 2225/41; H04R 1/02; H04R 25/00; H04R 25/603; H04R 25/652; H04R 25/456; H04R 1/1041; H04R 2460/11; G10L 25/63; A61B 5/6815; A61B 5/6803; A61B 5/165

See application file for complete search history.

(56) References Cited

U.S. PATENT DOCUMENTS

| | | | |
|---|---|---|---|
| 2017/0071551 | A1 | 3/2017 | Jain et al. |
| 2017/0112671 | A1 | 4/2017 | Goldstein |
| 2017/0289704 | A1 | 10/2017 | Frederiksen et al. |
| 2019/0149927 | A1 | 5/2019 | Zhang et al. |
| 2019/0253793 | A1 | 8/2019 | Pedersen et al. |
| 2020/0120433 | A1 * | 4/2020 | Serman ............ H04R 25/558 |
| 2020/0268265 | A1 * | 8/2020 | Walsh ............... A61B 5/6803 |

FOREIGN PATENT DOCUMENTS

| | | | |
|---|---|---|---|
| CN | 107801138 | | 3/2018 |
| CN | 110062318 | | 7/2019 |
| DE | 102009043775 | | 4/2011 |
| DE | 102009043775 A1 * | 4/2011 | ............ A61B 5/12 |
| DE | 102018204695 | | 12/2018 |
| EP | 3618456 | | 3/2020 |
| EP | 3618456 A1 * | 3/2020 | ............ A61B 5/165 |
| WO | WO 2011/038767 | | 4/2011 |
| WO | WO 2012/072141 | | 6/2012 |

OTHER PUBLICATIONS

Extended European Search Report for EP Patent Appln. No. EP19218516.3 dated Jun. 5, 2020.
PCT International Search Report and Written Opinion for International Appln. No. PCT/EP2020/084843 dated Feb. 11, 2021.
Extended European Search Report for EP Patent Appln. No. EP19218513.0 dated Mar. 19, 2020.
Non-Final Office Action for U.S. Appl. No. 17/740,299 dated Nov. 1, 2023.
Final Office Action for U.S. Appl. No. 17/740,299 dated Mar. 18, 2024.
Foreign Chinese office action dated Jun. 14, 2024 for Chinese Patent Application No. 202080087626.4.
Non-Final Office Action for U.S. Appl. No. 17/740,299 dated Jul. 12, 2024.
Foreign Chinese office action dated Jul. 31, 2024 for Chinese Patent Application No. 202080087211.7.
Non-Final Office Action for U.S. Appl. No. 17/740,299 dated Mar. 5, 2025.
Final Office Action for U.S. Appl. No. 17/740,299 dated Dec. 6, 2024.
Foreign Office Action for Chinese Patent Application No. 202080087211.7 dated Jan. 18, 2025.

* cited by examiner

SYSTEM COMPRISING A COMPUTER PROGRAM, HEARING DEVICE, AND STRESS EVALUATION DEVICE

RELATED APPLICATION DATA

This application is a continuation of International Patent Application No. PCT/EP2020/084812 filed on Dec. 7, 2020, which claims priority to, and the benefit of European Patent Application No. 19218516.3 filed on Dec. 20, 2019. The entire disclosures of the above applications are expressly incorporated by reference herein.

FIELD

The present disclosure relates to a system comprising a computer program, at least one hearing device worn by a user, and at least one stress evaluation device. The system is configured to measure a stress parameter related to stress of the user and determine an indication of stress based on the stress parameter.

BACKGROUND

Stress is the most common risk factor for a large variety of mental and physical diseases and health problems. Stress is associated with increased risk for cardio-vascular diseases, cancer, chronic pain, anxiety, depression, etc. Given these effects of stress on health, numerous techniques and methods have been applied to assess stress of an individual and/or population. The most used methods for assessing stress of an individual are conducting stress interviews and questionnaires and measuring biological processes regulated by stress exposure. However, most of the methods often lack details about origin of stress and cannot be performed in a real time and real life scenarios.

With the development of new technologies and personal devices, it is believed that in the future many people will perform daily activities having wearables including hearing devices. In future, one of the uses of hearing devices in combination with other wearables may be stress assessment and stress relief.

SUMMARY

It is an object of embodiments to provide a system which can determine stress of the system user.

It is a further object of embodiments to provide a system which can reduce stress of the system user.

It is a yet further object of embodiments to provide a system which can identify hearing problems of the system user.

Disclosed, in a first aspect, is a system comprising a computer program, at least one hearing device, and at least one stress evaluation device. The computer program is configured to be executed in an external computing device. The at least one hearing device is configured to be worn by a user. The at least one hearing device comprises one or more microphones, a processing unit, a speaker, and a wireless communication unit. The user wearing the at least one hearing device is in an environment. The environment is defined by an acoustic scene. The one or more microphones are configured to receive audio signals from audio sources in the environment and provide the audio signals to the processing unit. The processing unit is configured to apply processing parameters to thereby process the audio signals. The speaker is configured to provide the processed audio signals to the user. The at least one stress evaluation device is configured to be worn by the user and configured to measure a stress parameter related to stress of the user. The stress parameter is related to the acoustic scene. The at least one stress evaluation device is configured to communicate with the external computing device to send the measured stress parameter to the external computing device. The computer program is configured to determine an indication of stress of the user based on at least the stress parameter received from the stress evaluation device.

The computer program is configured to be executed in an external computing device. The computer program comprises instructions which, when the program is executed by the external computing device, may cause the external computing device to communicate with the hearing device of the system. The instructions are for determining an indication of stress.

The external computing device may be a server, such as a cloud server or an electronic device such as a smart phone, personal computer, laptop, etc. The server may be a remote device with a large computing power. The external computing device may comprise more than one computing units. The external computing device may refer to a cloud-computing platform available to many users over the Internet. The external computing device may, at the same time, be used for other purposes than the purposes of the disclosed system. The external computing device may comprise computational units as well as memory units.

The at least one hearing device may be an electronic device designed for multiple purposes ranging from wireless transmission to communication objectives, medical monitoring, fitness tracking, etc. The hearing device may be a hearing aid, headset, headphones, earphones, noise cancelling headset, hearable, cochlear implant, and the like. A user of the hearing device may be a person with normal hearing or it may be a person with any kind of hearing problems. The at least one hearing device is configured to be worn by the user.

The at least one hearing device comprises one or more microphones. The microphone(s) typically convert sounds from the environment into corresponding electrical signals. The one or more microphones may be arranged outside of the user's ear or they may be arranged inside the user's ear. The microphone(s) arranged outside of the user's ear or in the ear but facing the user's surroundings may receive sounds from the surroundings as well as the user's spoken voice. The microphone(s) arranged inside the ear canal may receive vibrations of the user's bone structures which occur when the user speaks. The received signal is then processed and may further be provided to the user via a speaker. The one or more microphones may include a boom microphone and/or an in the ear microphone. The in the ear microphone may be measuring vibrations generated when the user speaks.

The one or more microphones are configured to receive audio signals from audio sources in the environment. The audio signals are a representation of sound having frequencies in the audio frequency range from around 20 Hz up to around 20 KHz. The audio signals may be a voice of a person talking to the user of the hearing device or voices from a group of people, and/or audio content from an external device, e.g. music. The audio signals may be noise from the user's surroundings, etc.

The audio sources may be people talking, speakers playing music, sounds from traffic, noise from people's activities on the street, etc. The user wearing the hearing device is present or situated in an environment. The environments may be of different types, such as an office space, nature, street, user's home, museum, shopping mall, airport, etc. The environment is defined by an acoustic scene. The environment may also be defined by visual signals and visual arrangement of objects within the scene.

The acoustic scene may be characterized by a number of audio sources, their sound level, and their arrangement, geometry of a room, such as the area of the floor, the height of the walls, the number of people in the room/scene, reverberation, music, etc. The acoustic scene may also be characterized by a scenario of an event, such as a meeting, a cocktail party, a discussion in an office space, a discussion with a cashier, etc.

The audio signals are converted in the one or more microphones and provided to the processing unit. The one or more microphones and processing unit may be connected via electronic conducting lines configured to conduct electrical signals from the microphones to the processing unit.

The at least one hearing device comprises the processing unit. The processing unit may comprise a number of electronic components such as filters and amplifiers which may then modify the electrical signals received from the one or more microphones. The received electrical signals may be amplified by the processing unit. The processing unit may filter out any noise present in the sound received by the hearing aid and output clear and undistorted electric signals which the user wants to hear.

The processing unit is configured to apply processing parameters to thereby process the audio signals. The processing parameters may include amplification, attenuation, filtering, compression, echo management, speech recognition, noise cancellation, equalization, source separation and classification, beamforming and directionality of sounds, feedback cancellation, etc. The processing parameters may be adjusted by the user and/or may be adjusted automatically. The adjustment of the processing parameters may depend on the user's environment, the acoustic scene, and the audio signals received by the hearing device. The processing parameters may also depend on the user's hearing.

The at least one hearing device comprises a speaker, such as a loudspeaker, receiver or output transducer. The speaker may be in a direct communication with the processing unit via electric conducting lines thereby receiving the audio signals processed by the processing unit. The speaker converts the processed audio signals which are in electronic form into sound. The speaker is configured to provide the processed audio signals to the user, in the form of sound.

The at least one hearing device further comprises a wireless communication unit. The wireless communication unit may provide wireless connection between the at least one hearing device and another user's device which may be the user's smart phone, laptop, tablet, or similar. In the case of the at least one hearing device being a hearing aid for binaural hearing, the wireless communication unit may provide communication between the left and right hearing aid. The wireless communication unit may ensure communication between the at least one hearing device with external devices, e.g. computers being part of a cloud-computing platform or servers. The wireless communication unit may receive signals which are used for providing sound to the user via the speaker.

The system comprises at least one stress evaluation device configured to be worn by the user. The at least one stress evaluation device is further configured to measure a stress parameter. The at least one stress evaluation device may comprise one or more sensors (e.g. a heart rate sensor worn by the user) connected to a processor. Each of the sensors may perform measurements related to the user's physiological condition and provide the measurements to the processor configured to compile the received sensor measurements into the stress parameter. The at least one stress evaluation device may further be configured to perform various physiological measurements, such as electroencephalogram (EEG), electrocardiogram (ECG), electrooculography (EOG), temperature, skin resistance, skin conductance, beat rate, respiratory rate, blood volume pulse, electrodermal activity (EDA), etc., which are directly linked to stress of the user. The stress evaluation device may be a part of the at least one hearing device. It may be one of the microphones of the hearing device.

The at least one stress evaluation device is configured to communicate with the external computing device to send the measured stress parameter to the external computing device. For this purpose, the at least one stress evaluation device may comprise a wireless transmitter for establishing wireless communication with the external computing device. The at least one stress evaluation device may, alternatively, communicate the measured stress parameter to the at least one hearing device, and then the hearing device may communicate the stress parameter further to the external computing device. This, in particular, may be the case if the stress evaluation device is a part of the hearing device.

The stress parameter is related to stress of the user. The user may be stressed because of inability to react promptly and adequately in the given situation. A reason for not being able to react properly may be degraded hearing of the user. Stress of the user may also be related to the acoustic scene. Namely, the acoustic scene may comprise several noise sources which may cause stress of the user.

Therefore, the measured stress parameter is also related to the acoustic scene. The more complex the acoustic scene is, the more stress it may cause in the user, as the user may be deconcentrated by many factors present in the acoustic scene. Namely, a complex acoustic scene puts a high cognitive demand on the user. The complex acoustic scene may comprise more than one audio source. However, the same acoustic scene may be perceived differently by different users, depending on the users' hearing, for instance. Additionally, the same acoustic scene may be perceived differently by the same user at two different points in time depending on the user's mood and/or the user's progressing hearing deficit. The relation between the acoustic scene and stress originates from an, e.g. unconscious, acoustic scene analysis performed by the user. The user being in an acoustic scene may want to identify arrangement and classification of audio sources and acoustic events, their possible motion (e.g. a person walking, a train accelerating, etc.), speaker identification, etc. The more details about the acoustic scene which are to be identified, the more complex, and demanding for the user it is.

In the present context, stress of the user may be related to the user's hearing capabilities, such as in a specific acoustic scene of a specific environment. If the user already has a hearing loss, stress of the user may occur if the hearing device does not sufficiently account for the user's hearing loss. This may be due to incorrect settings in the hearing device, incorrect mode, if the user's hearing loss has changed etc. If the user is not a hearing device user, and the user does not yet have a detected hearing loss, stress of the user may occur if a hearing loss of the user has developed. Stress of the user may also relate to the current signal processing in the hearing device, i.e. to the processing parameters.

In the present context, the term "stress" is to be interpreted as a load on the user and the user's subjective perception and understanding of the acoustic scene. It may also be interpreted as cognitive load, i.e. the degree of concentration required for the user to correctly understand current or present audio signals. When the acoustic scene reaches a certain level of complexity, the user may unconsciously adapt/use his/her abilities to meet the challenge. When the acoustic scene is considered by the user as exceeding the available abilities and resources, stress would appear. Stress may refer to perceptually induced variations on the production of speech. Stress may refer to increased pulse, heart rate, and variations thereof. Stress may refer to changes in body temperature. Stress may refer to changes in skin resistance of the user, a galvanic skin response, and/or a skin conductance response. Stress may relate only to the usage of the hearing device and the user's experience of the hearing device. For instance, stress of the user may be increased if the hearing device does not appropriately compensate for the user's hearing deficit.

The computer program is configured to determine an indication of stress of the user based on at least the stress parameter received from the stress evaluation device. The external computing device receives the measured stress parameter from the stress evaluation device and provides it to the computer program. The computer program may perform a plurality of instructions in order to determine the indication of stress. The plurality of instructions may include various mathematical models, physiological and behavioural models, and manipulation of the measured stress parameter in order to determine the indication of stress. The computer program may include one or more look-up tables with various stress parameters and corresponding indications of stress. Depending on a type of the measured stress parameter, the computer program may perform different instructions. Namely, the computer program may comprise one set of algorithms when determining the indication of stress starting from, e.g., user's speech as the measured stress parameter. Different set of algorithms, such as Maxwell relations of thermodynamics applied to the human system, may be performed if the measured stress parameter is a combination of, e.g., heart rate, skin resistance, and blood pressure. The computer program determines the indication of stress and sends it to the external computing device which may store the indication of stress and the corresponding measured stress parameter.

The indication of stress is to be interpreted as a stress quantifier describing a level of stress of the user. The indication of stress may be compared with one or more threshold stress values in order to determine whether the user is stressed or not, or which stage of stress the user is at. The computer program may have a plurality of predefined indications of stress. Even small variations in stress parameter may result in the same indication of stress.

The processor may have pre-programmed algorithms for determining a cognitive load of the user. The generated indication of stress may be based on the performed physiological measurements and/or parameters obtained by the one or more sensors. It is an advantage that the hearing device can apply specific signal processing in order to compensate for stress of the user or to decrease stress level.

The indication of stress in various acoustic scenes may be used in a feedback-loop where gain and directionality in the hearing device is adjusted continuously. If a positive result is obtained, i.e. the indication of stress drops, then the adjustment was correct and further adjustments in the same direction may be applied. If the indication of stress raises, the adjustment may be rolled back and/or other adjustments may be introduced.

An increase in average stress level on a monthly timescale not explained by more complex acoustic environments or increasing hearing loss could be caused by more severe health issues, e.g. cognitive decline (dementia), insomnia, or other physiological problems. By assessing information about the stress of the user, it is possible to timely resolve issues and thereby improve the user's everyday life.

In some embodiments, the at least one hearing device may be configured to communicate with the external computing device. The external computing device may be configured to send the indication of stress of the user to the at least one hearing device. Both the hearing device and the external computing device may have communication units connected to each other, typically via internet. The communication may be two-way, i.e. the hearing device may both send and receive data from the external computing device, and vice versa. The hearing device sends stress parameters, and may also send received audio signals, current settings of the hearing device, etc. By receiving the indication of stress from the external computing device, the hearing device may asses hearing capabilities and abilities of the user and thereby provide the best user experience. Furthermore, the at least one hearing device can provide information and indications of hidden hearing loss of the user.

In some embodiments, the external computing device may be configured to send a suggestion to the at least one hearing device to perform an action. The suggestion may be based on the determined indication of stress of the user. The action may include optimization of audio signal processing in the hearing device. The computer program may be configured to determine the suggestion. The suggestion may aim to reduce the stress of the user by suggesting appropriate changes in audio signal processing in the hearing device so that the user differently perceives the acoustic scene. Having the external computing device determining and providing the suggestion to the hearing device to perform the action, processing power demand of the hearing device are decreased.

In some embodiments, the processing unit of the at least one hearing device may be configured to decide whether to perform the action. The decision may be based on the received audio signals and the indication of stress of the user received from the external computing device. In cases when stress of the user is below a predefined threshold, the decision of the processing unit of whether to perform the action may be a decision not to perform any action. In cases when stress is equal or above the predefined threshold, and/or when the acoustic scene changes, the decision of the processing unit of whether to perform an action may be a decision to perform an action, such as the action of adjusting the processing parameters of the processing unit. Alternatively, the decision may be a "delta-decision", i.e. based on changes in the indication of stress over time or a sudden change even though the indication of stress is not over a certain threshold. The decision may also be based on a relative indication of stress, e.g. what is the current indication of stress relative to an average of the specific user. The action may be a change in the processing parameters, a notification to the user, and/or sending the indication of stress to an external device, e.g. the user's phone, cloud-computing platform, server, database. The action may be to make a data point as input for future decisions in the hearing device, e.g. to perform different processing next time, or only change processing parameters after a number of similar observations.

The received audio signals may be analysed by the processing unit to thereby reconstruct the objective acoustic scene, at least partly. The indication of stress, calculated and received from the external computing device, is also related to the acoustic scene as perceived by the user, i.e. the subjective acoustic scene. When making the decision, the processing unit may compare the subjective acoustic scene perceived by the user and the objective acoustic scene. In some cases, the acoustic scene may objectively be complex, e.g. a background noise is extremely high, and therefore stress of the user may be reasonable and expected. In these scenarios, the processing unit may perform no action automatically. By having the processing unit performing an action based on the received audio signals and the indication of stress, optimal settings and adjustments for a particular user being in a particular environment are provided.

In some embodiments, the action may comprise adjusting the processing parameters based on the decision. The processing parameters may continuously be adjusted based on updated decisions. In some embodiments, the computer program may determine adjustment of the processing parameters. In this embodiment, the hearing device may provide current settings to the external computing device and the computer program may use those in determining the adjustment of the processing parameters. The adjustment processing parameters may be provided to the hearing device by the external computing device. By adjusting the processing parameters based on the decision, user's stress can be reduced. For instance, for the wearer of the hearing device, e.g. headphones, the indication of stress can be used for performing the action of automatic volume amplification or volume decrease. Alternatively, the action may be a suggestion to the wearer to increase/decrease the volume of the sound. In another example, for the wearer of the hearing device such as a hearing aid, the indication of stress can be used for performing the action of mode switching. Alternatively, the action may be a suggestion to the wearer to use other operational modes or settings in the hearing aid, to get more amplification, to visit a healthcare professional, or to provide suggestion on how to optimize the current situation. Changing the mode or adjusting setting of the hearing device may optimize sound processing in the hearing device and thereby reduce stress of the user and/or improve hearing.

In some embodiments, the at least one hearing device may comprise the at least one stress evaluation device. In this embodiment, the hearing device may also communicate the stress parameter to the external computing device. The communication between the hearing device and the external computing device may be established via the Internet. In addition to the stress parameter, other data may be communicated through the same data channel. The other data may be the audio signals, control signals, processing parameters, current settings of the hearing device, etc. By having the stress evaluation device being part of the hearing device, the system is simplified.

In some embodiments, the indication of stress may be determined based on at least the user's speech detected by the one or more microphones of the at least one hearing device. According to this embodiment, signals detected by the hearing device microphone(s) are the measured stress parameter and includes the user's speech. The detected signals are then sent to the external computing device. The user's speech may be detected by a boom microphone arranged close to the user's mouth. The user's speech may be detected by a microphone arranged in or at the hearing device, such as a microphone behind the ear, and/or in the ear, such as at the concha of the ear or in the ear canal etc. The external computing device may isolate the speech from other sounds picked up by the microphone and analyse it further. Stressed speech may be defined as the speech produced under any condition that causes the speaker to vary speech production from neutral condition. The speech may be affected by the mental state of the speaker/user and can thus be used for generation of the indication of stress. The speech may be analysed by analysing various parameters such as a speech speed, speech length, time limitation, tempo, pitch, content of speech, fundamental frequency and formants, stuttering, etc. For instance, in the low stress conditions, the user normally speaks calmly using a clear voice with normal speed, conversation/talking is not urged to speed up its performance. The external computing device then generates the indication of stress which corresponds to acoustic scenes where the user has no stress. In the high stress conditions (e.g. presence of white noise, ambulance sound, etc.), the user may talk fast, using short sentences and an urgent tone, make mistakes and repeat some of the words, etc. The external computing device may generate the indication of stress which corresponds to acoustic scenes where the user feels stressed. When the external computing device generates the indication of stress which shows that the user is stressed, received audio signals from the environment will be analysed in order to make a decision whether to perform an action or not. It is advantageous to determine the indication of stress based on the user's speech as the speech is affected by the environmental conditions. Therefore, it is possible to determine if the user is stressed due to, e.g. exposure to high noises or simply because the user has a hearing deficit which is not compensated for. Furthermore, by identifying stress by analysing the user's speech detected by the one or more microphones, complexity of the system is reduced as the microphones which are already a part of the hearing device are used as the stress evaluation device, i.e. for the user's speech detection and there is no need for additional sensors for stress detection.

When comparing two speech signals and their spectrograms, one uttered with neutral emotion and the other with anger emotion, it is possible to identify some visible differences especially in terms of signal duration and amplitude. The speech uttered with anger emotion may have a duration less than that uttered with neutral emotion. The average amplitude of the signal may have a higher value in case of the speech signal uttered with anger emotion. The spectrograms may show that the frequencies have shifted upward or have higher values in the speech signal uttered with anger emotion compared to the speech uttered with neutral emotion.

In some embodiments, the stress evaluation device may comprise a temperature sensor, a heart rate sensor, a skin resistance sensor, and/or the one or more microphones. The stress evaluator may also comprise an electrodermal activity sensor for measuring changes in skin conductance resulting from the sympathetic nervous system activity and being one of stress indicators. The stress evaluator may further comprise a respiratory rate sensor. The sensors may be distributed at various places on the user's body. Skin conductance response measured by the skin resistance sensor is a measure that is traditionally associated with workload and especially with arousal states accompanied by mental effort and emotions. Higher workload normally yields higher number of skin conductance responses. In an embodiment, in which the stress evaluation device is a part of the hearing device, the sensors may be arranged on the outside of the hearing device to thereby be in a direct contact with the user's skin and measure temperature, skin resistance, and/or heart rate of the user. Heart rate normally increases when the user is stressed. Temperature of different body parts may be different when the user is exposed to stress. The system may therefore comprise a plurality of stress evaluation devices in a form or a plurality of temperature sensors place on different places of the user's body. Assessing stress using body temperature, heart rate, skin resistance, and/or speech is inexpensive and non-intrusive, as all these parameters can be obtained without the user noticing it. Furthermore, having multiple and different sensors to perform measurements which are used in determination of the indication of stress, the accuracy of the determination is improved. By combining a plurality of uncorrelated sensors, the confidence of the determined indication of stress in increased, as multiple sensors may provide more reliable data than a single one.

In some embodiments, the indication of stress may comprise providing a request to the user to adjust the processing parameters of the at least one hearing device. The hearing device, which receives the indication of stress from the external computing device, may communicate with, e.g. the user's phone and send a message to the phone about the request encoded in the indication of stress. The user may decide whether to fulfil the request by switching between different operational modes. Sending the request may be the action performed by the processing unit. The request may be for instance a suggestion to the user to change/use different listening features. By sending the request to the user to adjust the processing parameters the user has a freedom to decide whether to make changes in the processing parameters or not. This improves user experience of the hearing device.

Alternatively, the indication of stress may comprise providing instructions to the hearing device to adjust the processing parameters. In this embodiment, the hearing device may change the processing parameters right after receiving the indication of stress from the external computing device. In some embodiments, the processing parameters may comprise a first processing parameter and a second processing parameter. The processing unit may then be configured for changing from the first processing parameter to the second processing parameter based on a detection that the acoustic scene changes from a first acoustic scene to a second acoustic scene. The processing unit may reconstruct the acoustic scene based on the received audio signals. The first acoustic scene may be an acoustic scene with no or very little noise, such as user's home. The second acoustic scene may be an acoustic scene characterized with a high level of noise, such as busy street. If the user relocate from home to the busy street, the processing unit may, based on the detected noise level, apply noise cancellation to the received audio signal. Namely, the change of the processing parameters based on the change of the acoustic scene may prevent the user's stress. The change may also be based on the indication of stress, received audio signals, user's input, or some other parameter. The change in the processing parameters, may be changed either before or after the indication of stress is generated. This change helps the user not to feel stressed when changing the acoustic scene.

In some embodiments, the at least one hearing device may further be configured for forwarding at least a part of the user's speech to the external computing device. The external device may then perform processing of the user's speech either alone or in addition to the stress parameter received from the at least one stress evaluation device. The processed speech may be used for calculating the indication of stress. Alternatively, the speech processing may be performed instead of the processing unit of the hearing device. Speech processing may be highly demanding in terms of processing power. By forwarding the user's speech to the external device demands on the processing unit of the hearing device are relaxed.

In some embodiments, the external computing device may comprise a database comprising historical data, the historical data relating to the user's perceptual hearing and/or a general perceptual hearing. The indication of stress may be determined based on the historical data. In the determination of the indication of stress, the historical data may be used in addition to the measurements and the stress parameter obtained by the stress evaluation device. Namely, the indication of stress may be determined based on a difference between the measured stress parameter and one or more expected stress parameters. The expected stress parameters may form part of the historical data. Perceptual hearing includes both detecting a sound wave with the ear of a listener and interpretation of the detected sound signal by the brain of the listener. The general perceptual hearing relates to an average perceptual hearing which may be based on perceptual hearing of a plurality of listeners. Perceptual hearing may be defined for a specific environments and acoustic scenes.

The historical data may relate to the user's perceptual hearing in similar situations, i.e. in similar environments defined by similar acoustic scene and/or to perceptual hearing of other users of hearing devices. The historical data may contain indications of stress of a hearing device user and information about the environment. The historical data related to the user may also be used to determine changes in the user's hearing in long term, i.e. if the hearing has improved/degraded/changed in any way. A part of the historical data may be a comparison between a current stress measurement and another measurement from another point of time for similar environment. The user may often be in the same or similar situations. If the assessment of stress changes over time in situations of comparable complexity, the assessment of stress over time may provide an indication of progressing hearing deficit. Additionally, the historical data may comprise perceptual hearing of, e.g., 100 hearing device users being in the same environment with a similar acoustic scene. These data may then be compared with the generated indication of stress of the user being in the same environment. If the comparison reveals that the user's stress is different from the historical data of other users, it may be a sign of potential hearing problems of the user. In other words, through a population of hearing device users, an average perceptual hearing for acoustic scenes with different complexity could be obtained. This average could be used as a reference for the current user in the current situation. If the user is a long-term user, the historical data may comprise individual data of this particular user. For new users, the historical data may be based on general data, i.e. data from other users with a similar profile (defined by age, hearing deficit, etc.).

In some embodiments, the computer program may be configured to detect a hearing deficit of the user, and/or an uncompensated hearing loss of the user, and/or a change in the hearing capability of the user. The historical data may define one or more expected stress parameters. The expected stress parameters may be relative to the complexity of the acoustic scene. If one or more expected stress parameters comprise expected stress level parameter, by determining the difference (d) between the actual stress level (actual stress) and the expected stress level (expected stress) it can be determined whether the user is challenged or not. The user is challenged if the difference between actual and expected stress is above zero. The challenge may indicate uncompensated hearing loss and/or deficit, i.e. if $d=$ actual stress−expected stress is above zero, the computer program may report uncompensated hearing loss of the user. Such difference may be tracked over a predetermined time span in order to calculate an average value of the difference. The predetermined time span may be one or more weeks, one or more months, or one year. The average value may provide a more accurate estimate on the hearing loss or deficit.

In this embodiment, the computer program may be configured to determine or suggest a solution/compensation to the detected hearing deficit or hearing loss of the user. The suggestion/solution/compensation may then be communicated from the external computing device to the at least one hearing device in a form of a suggestion to the hearing device to perform an action. The hearing deficit, and/or the uncompensated loss of the user, and/or a change in the hearing capability of the user may be detected by comparing the received audio signals and the indication of stress of the user. The received audio signals may be a voice of a person talking to the user. The indication of stress may be determined based on the user's speech. The processing unit may compare the content of the person's speech with the content of the user's speech. If the user's speech does not correspond to the speech of the person, it may be a sign of hearing problems of the user. By detecting the hearing problems, the user may be alerted on time and without going to a doctor about the problems. Prevention of further problems may also be achieved.

In some embodiments, the hearing deficit of the user, and/or the uncompensated hearing loss of the user, and/or a change in the hearing capability of the user may be detected based on the acoustic scene and the indication of stress. Information about the acoustic scene may be provided to the external computing device by the hearing device or by a user's personal device which may also be in communication with the external computing device. These hearing problems may be detected either by the external computing device or by the hearing device. The processing unit of the hearing device may restore details about the objective acoustic scene from the received audio signals. Based on the objective acoustic scene the processing unit may predict the user's stress in the given situation. If this prediction does not match the indication of stress determined by the computer program with the prediction of the processing unit, it may be a sign of the hearing deficit and/or hearing loss of the user. Furthermore, the processing unit may predict the user's stress based on previous indications of stress generated in similar situations. Machine learning algorithms may be used for predicting the user's behaviour in particular situations and thereby detect change in the hearing capability of the user. Alternatively, the external computing device may predict the user's stress based on previous indications of stress generated in similar situations. In detection of the hearing problems of the user, the external computing device may use historical data stored in the database. By detecting the hearing problems based on the acoustic scene and the indication of stress particulars about the problems can be identified, such as if the user has a problem of hearing sounds coming from behind the user, or in hearing low frequency sounds, etc.

In some embodiments, the at least one hearing device may be a hearing aid configured to compensate for a hearing loss of the user. The hearing aid may be any type of a hearing aid, such as a behind the ear hearing aid, in the ear hearing aid, or the like. The hearing aid may be configured for binaural hearing. According to some embodiments, having the hearing device in the form of a hearing aid, additional functionalities of the hearing aid can be allowed, hearing problems of the user can be tracked, and an automatic control of the sound processing based on the hearing loss can be performed.

In some embodiments, the external computing device may be configured to receive a data signal comprising acoustic scene information, the computer program being configured to process the data signal and generate the indication of stress of the user based on the data signal. The data signal may be received from the user's smart phone and may give particulars about the scene the user is in. The data signal may comprise GPS information, a video of the acoustic scene, and a picture of the acoustic scene or at least a part of the environment the user is in. The data signal may further comprise a Wi-Fi signal related to the environment the user is in, a size of the room the user is in, a number of people in the room, a number of sources in the acoustic scene, etc. The audio signals received by microphones of the hearing device may have some information about the scene encoded therein. By receiving the data signal related to the acoustic scene the external computing device may reconstruct the objective acoustic scene with a high precision and thereby perform the decision with improved accuracy.

Disclosed, in a second aspect, is a method performed by a system comprising a computer program, at least one hearing device, and at least one stress evaluation device. The computer evaluation device is configured to be executed in an external computing device. The at least one stress evaluation device is configured to be worn by a user. The at least one hearing device is configured to be worn by the user. The user is in an environment defined by an acoustic scene. The hearing device comprises one or more microphones, a processing unit, a speaker, and a wireless communication unit. The method comprises receiving, at the one or more microphones of the at least one hearing device, audio signals from acoustic sources in the environment. The method further comprises providing the received audio signals to the processing unit, the processing unit applying processing parameters to thereby process the audio signals and provide them to the speaker. The at least one stress evaluation device measures a stress parameter related to stress of the user, the stress parameter being related to the acoustic scene. The measured stress parameter is then provided to the external computing device. The computer program determines an indication of stress of the user based on at least the stress parameter received from the stress evaluation device.

The method according to the second aspect utilizes the system according to the first aspect. The skilled person would therefore readily understand that any feature described in combination with the first aspect could also be combined with the second aspect, and vice versa. Accordingly, the remarks set forth above with reference to the first aspect are equally applicable on the second aspect.

The present disclosure relates to different aspects including the system described above and in the following, and corresponding method, each yielding one or more of the benefits and advantages described in connection with the first mentioned aspect, and each having one or more embodiments corresponding to the embodiments described in connection with the first mentioned aspect and/or disclosed in the appended claims.

BRIEF DESCRIPTION OF THE DRAWINGS

The above and other features and advantages will become readily apparent to those skilled in the art by the following detailed description of exemplary embodiments thereof with reference to the attached drawings, in which.

DETAILED DESCRIPTION

Figure 1:
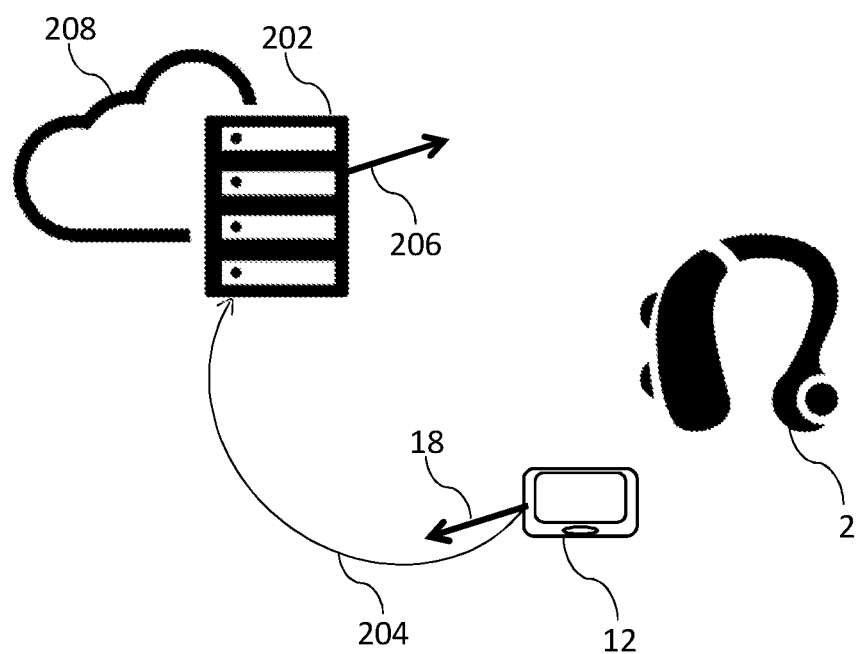
FIG. 1 schematically illustrates an exemplary system according to some embodiments, FIG. 2 schematically illustrates an exemplary hearing device, FIG. 3 schematically illustrates an exemplary environment with a user wearing a hearing device and a stress evaluation device, FIG. 4 schematically illustrates another exemplary system according to some embodiments, FIG. 5 schematically illustrates an exemplary method executed by the system of FIG. 1 or FIG. 4, FIG. 6 schematically illustrates yet another exemplary system according to some embodiments.

Various embodiments are described hereinafter with reference to the figures. Like reference numerals refer to like elements throughout. Like elements will, thus, not be described in detail with respect to the description of each figure. It should also be noted that the figures are only intended to facilitate the description of the embodiments. They are not intended as an exhaustive description of the claimed invention or as a limitation on the scope of the claimed invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout, the same reference numerals are used for identical or corresponding parts.

FIG. 1 schematically illustrates an exemplary system 200 comprising a computer program configured to be executed in an external computing device 202, at least one hearing device 2, and at least one stress evaluation device 12. The at least one hearing device 2 is configured to be worn by a user. The user is situated in an environment characterized by an acoustic scene. The at least one stress evaluation device 12 is also configured to be worn by the user. The at least one stress evaluation device 12 is configured to measure a stress parameter 18 related to stress of the user. The stress parameter 18 is also related to the acoustic scene. The at least one stress evaluation device 12 is configured to communicate with the external computing device 202, preferably via a first wireless communication link 204 and to send the measured stress parameter 18 to the external computing device 202. The computer program is configured to determine an indication of stress 206 of the user based on at least the stress parameter 18 received from the stress evaluation device 12. The external communication device 202 may be a part of a cloud-computing platform 208.

Figure 2:
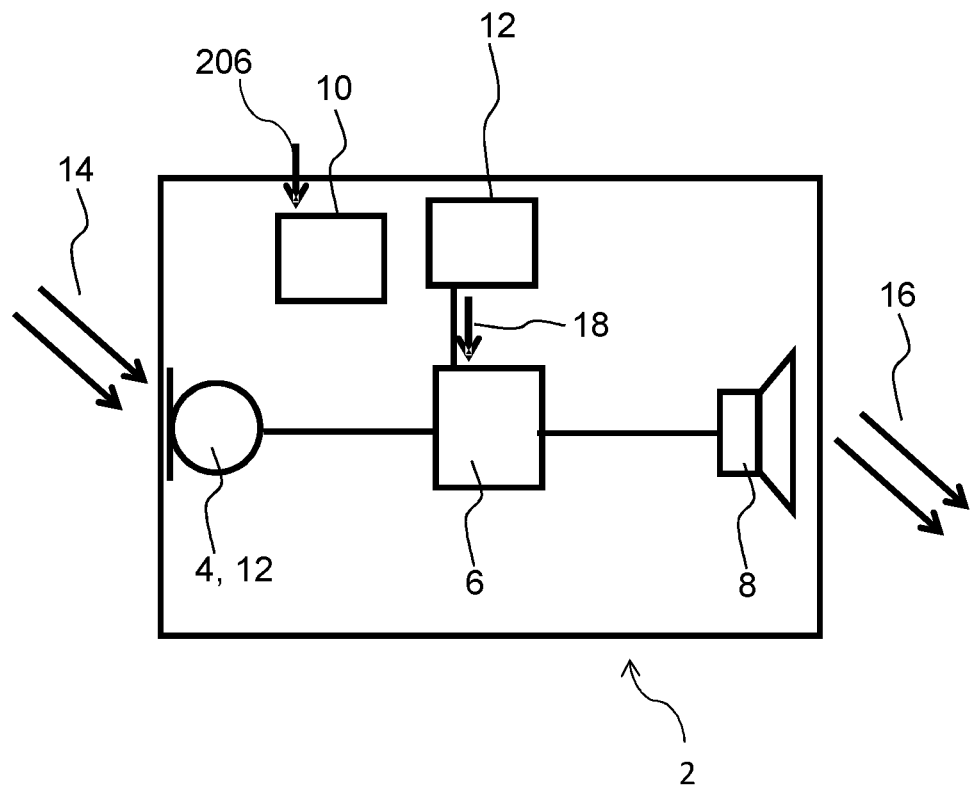

FIG. 2 schematically illustrates an exemplary hearing device 2. The hearing device 2 comprises a microphone 4, a processing unit 6, a speaker 8, and a wireless communication unit 10. The hearing device may also comprise a stress evaluation device 12. The hearing device 2 may comprise more than one microphone 4. The microphone 4 is configured to receive audio signals 14 from audio sources in the environment and provide the audio signals 14 to the processing unit 6. The processing unit 6 is configured to apply processing parameters to thereby process the audio signals 14. The speaker 8 may be directly connected to the processing unit 6 and the processing unit 6 may provide the processed audio signal to the speaker 8. The speaker 8 may then convert the processed audio signal into a sound for the user, i.e. the speaker 8 is configured to provide the processed audio signals 16 to the user. The stress evaluation device 12, being part of the hearing device 2 in the present embodiment, may be configured to generate a stress parameter 18, the stress parameter 18 is related to the stress of the user and to the acoustic scene. The processing unit 6 may be configured to decide whether to perform an action, the decision being based on the received audio signals 14 received from the environment and the indication of stress 206 of the user received from the external computing device (not shown) via the wireless communication unit 10. The stress evaluation device 12 may comprise a temperature sensor, a skin resistance sensor, or similar. In some embodiments, the microphone 4 may serve the purpose of the stress evaluation device 12.

Figure 3:
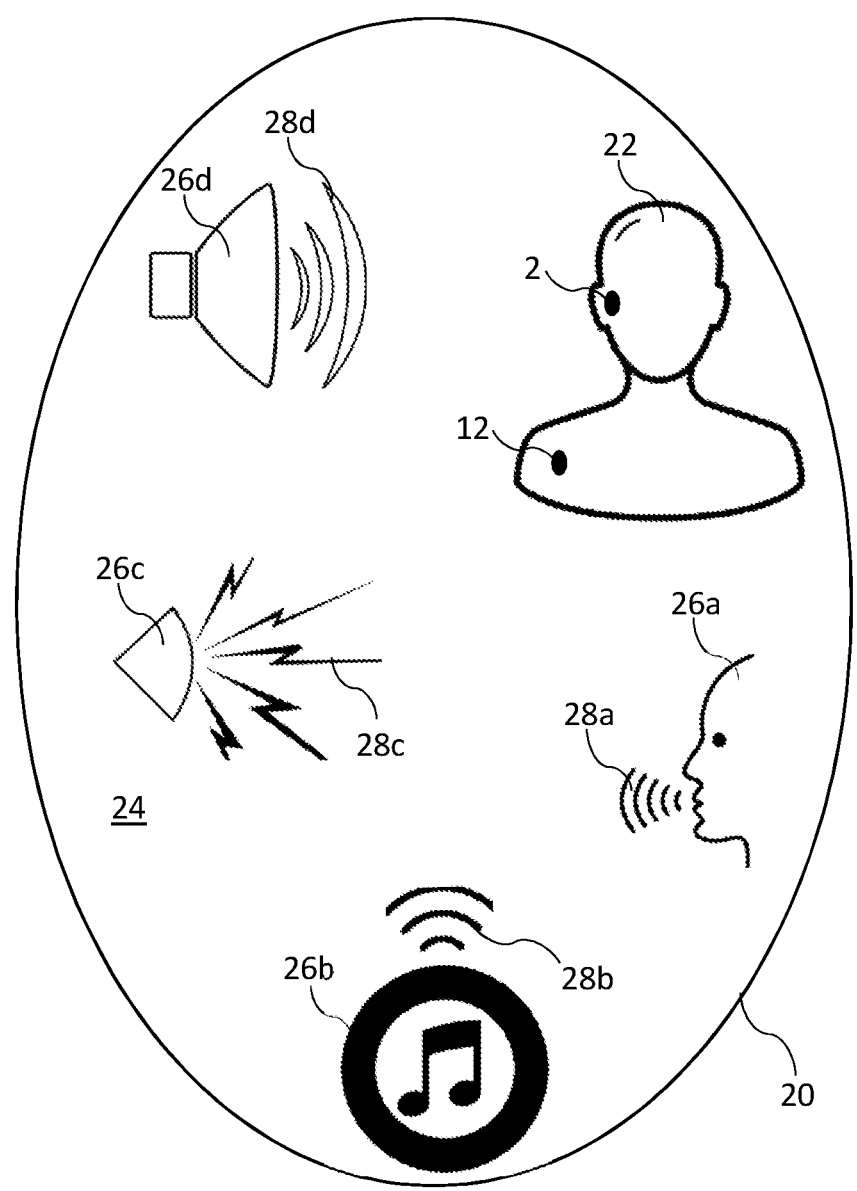

FIG. 3 schematically illustrates an exemplary environment 20 with a user 22 wearing a hearing device 2 and a stress evaluation device 12. The environment 20 is defined by an acoustic scene 24. The acoustic scene 24 comprises a plurality of audio sources 26, such as a person talking 26a, music source 26b, noise source 26c, loudspeaker 26d. Each of the audio sources 26a, 26b, 26c, and 26d generates a corresponding audio signal 28a, 28b, 28c, and 28d. The environment 20 may also comprise a plurality of visual sources which contribute to the user's cognitive load, attention, and therefore stress. Some of the audio sources, e.g. the person talking 26a and the loudspeaker 26d at the same time represent the visual sources as the user 22 may make notice of them while being in the environment. The arrangement of the audio sources 26a, 26b, 26c, and 26d may also affect the user's stress. For instance, if the noise source 26c is in a close proximity of the user 22, the user's stress level may be increased compared to the situation if the noise source 26c was far away. The hearing device 2 receives the audio signals 28a, 28b, 28c, and 28d via the one or more microphones (not shown). The audio signals 28a, 28b, 28c, and 28d are then processed by the processing unit of the hearing device 2. The processing unit may reconstruct the acoustic scene 24 and determine its complexity based on the received audio signals 28a, 28b, 28c, and 28d from the received acoustic signals 28a, 28b, 28c, and 28d.

Figure 4:
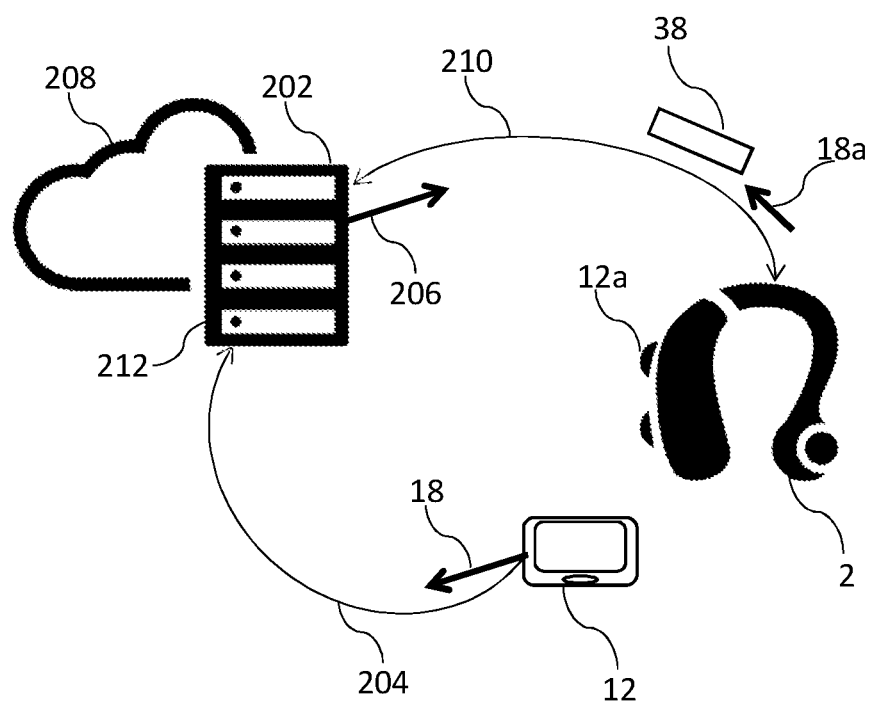

FIG. 4 schematically illustrates another exemplary system 200 comprising a computer program configured to be executed in an external computing device 202, at least one hearing device 2, and at least one stress evaluation device 12. In this embodiment, the hearing device 2 may be configured to communicate with the external communication device 202, preferably via a second wireless communication link 210. The second communication link 210 may be two-way communication link such that the hearing device 2 may send data to the external computing device 202 as well as the external computing device 202 may send data to the hearing device 2. The external computing device 202 may send the indication of stress 206 to the hearing device 2. The hearing device 2 may simultaneously be connected with more than one external computing device 202. The data sent from the hearing device 2 may include packages 38 comprising received audio signals. Additionally, the hearing device 2 may comprise another stress evaluation device 12a for measuring another stress parameter 18a, such as the user's speech. The hearing aid 2 may then send corresponding measurements of the stress parameter 18a from the stress evaluation device 12a to the external computing device 202. The packages 38 together with the corresponding stress parameter 18a may therefore relate to users' perceptual hearing for a given environment. These data may be used for building up a database 212 with historical data in the external computing device 202. The external computing device 202 may communicate with other hearing devices used by other users (not shown) which can then further contribute to the database 212 and historical data. The external computing device 202 may then send these historical data to the hearing device 2 through another or the same communication channel 210. The processing unit may then generate the decision based on the historical data. In some embodiments, the sensor evaluation device 12 may be connected to the hearing device 2, either wirelessly or through a wired connection. Both the hearing device 2 and the stress evaluation device 12 may be connected to a user's smart phone.

Figure 5:
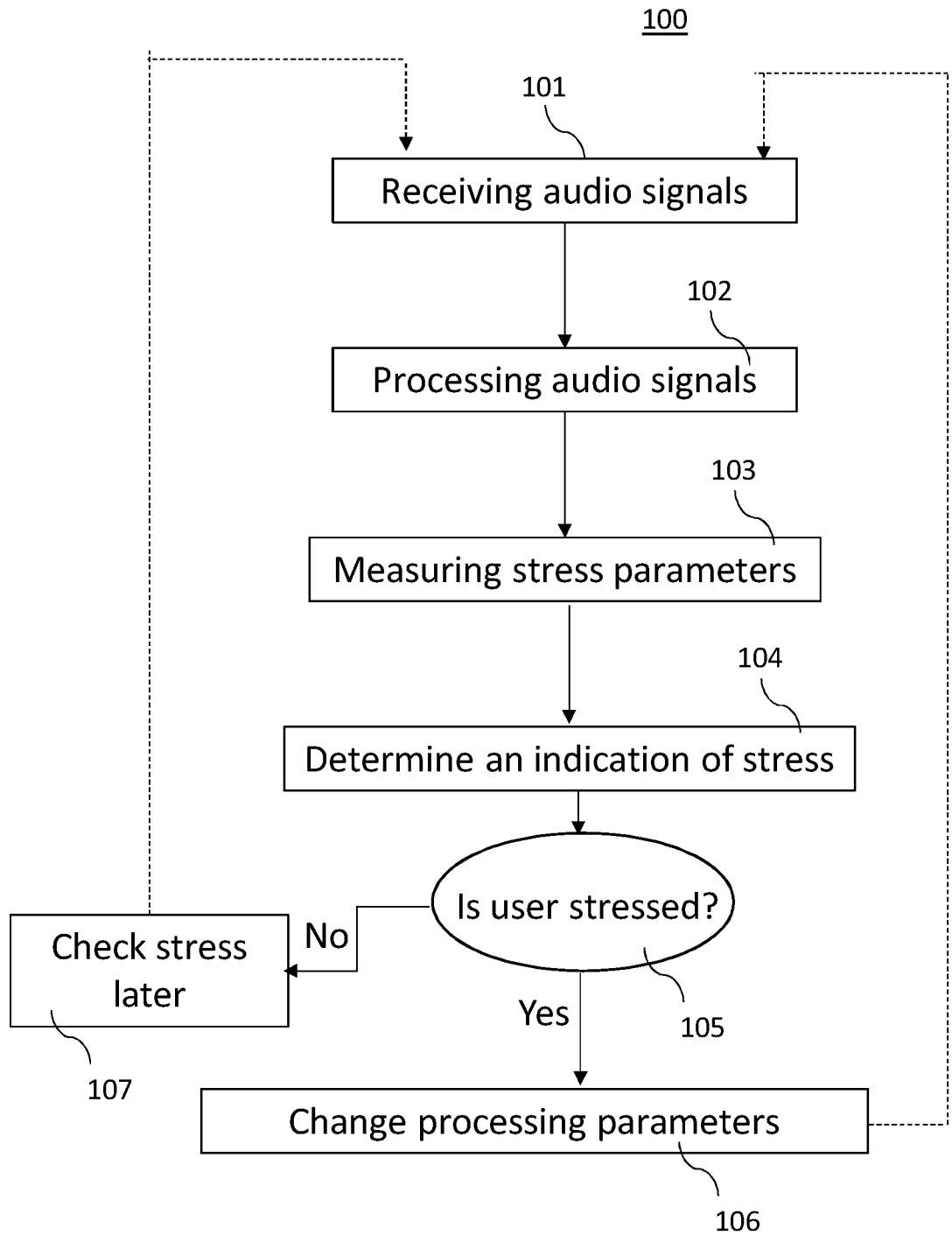

FIG. 5 schematically illustrates an exemplary method 100 executed by the system shown in FIG. 4. The method 100 comprises receiving 101 audio signals at the one or more microphones of the hearing device. The audio signals originate from the acoustic sources arranged in the environment. The method further comprises providing the received audio signals to the processing unit (not shown). The processing unit then applies processing parameters to thereby process 102 the audio signals and provide them to the speaker. The stress evaluation device then measures 103 a stress parameter related to stress of the user which is then provided to an external computing device. The method further comprises determining 104 an indication of stress of the user by a computer program executed on the external computing device, stress of the user being related to the acoustic scene. The external computing device may determine whether the user is stressed, based on the determined indication of stress. The indication of stress and the received audio signals may be compared 105 with a predetermined criteria and the result of the comparison may be that the user is not stressed. The processing unit may then check later again 107 whether the user is stressed, by performing the same steps again. If the outcome of the comparison is positive, i.e. the user is stressed, the processing unit may change 106 the processing parameters in order to reduce the stress. After the processing parameters are changed the method 100 may be performed again in order to check whether the change in the processing parameters resulted in reduction of stress. If stress is reduced but the user is still stressed the processing parameters may be changed further. If stress of the user is increased the processing parameters may need to be reset to previous values. Alternatively, the external computing device may obtain, from the hearing device, the audio signals received by the microphones. The computer program may then, based on the audio signals in combination with the determined indication of stress, generate a suggestion for the hearing device user about a change in processing parameters.

Figure 6:
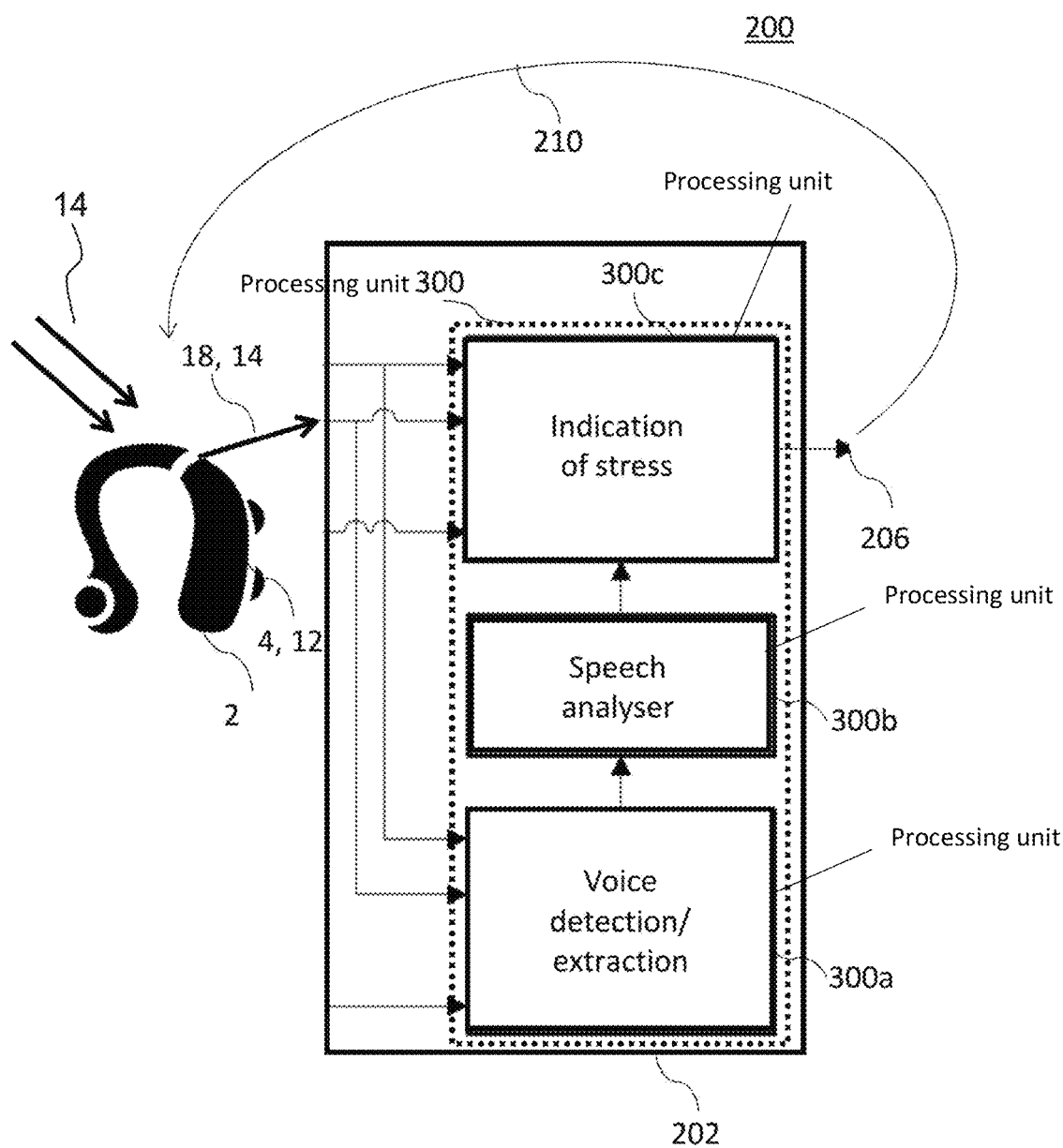

FIG. 6 schematically illustrates yet another embodiment of the system 200. In this embodiment, the one or more microphones 4 of the hearing device 2 are at the same time the stress evaluation device 12. The hearing device 2 receives the acoustic signals 14 from the environment. The acoustic signals 14 may comprise the user's own voice. In this embodiment, the acoustic signals 14 serve as the stress parameter 18 which is sent from the hearing device 2 to the external computing device 202. A computer program 300 in the external computing device 202 may comprise several algorithms 300a, 300b, 300c performing different instructions. The computer program 300 receives the stress parameter 18 and at first performs the user's voice detection and extraction from the received audio signals 14 in a voice detection/extraction algorithm 300a. The computer program then performs speech analysis in a speech analyser algorithm 300b. The speech analyser algorithm 300b sends its analysis to an indication of stress algorithm 300c which is configured to determine the indication of stress 206 based on the input from the speech analyser algorithm 300b and the stress parameter 18, i.e. the received acoustic signals 14 sent from the hearing device 2. The indication of stress 206 is then sent to the hearing device 2 via the second communication link 210. The computer program 300 may also determine a suggestion for the hearing aid 2 to change the processing parameters in case that the indication of stress 206 shows that the user is stressed. The suggestion may be determined based on the received acoustic signals 14 which have information about the acoustic scene encoded therein.

Figure 7:
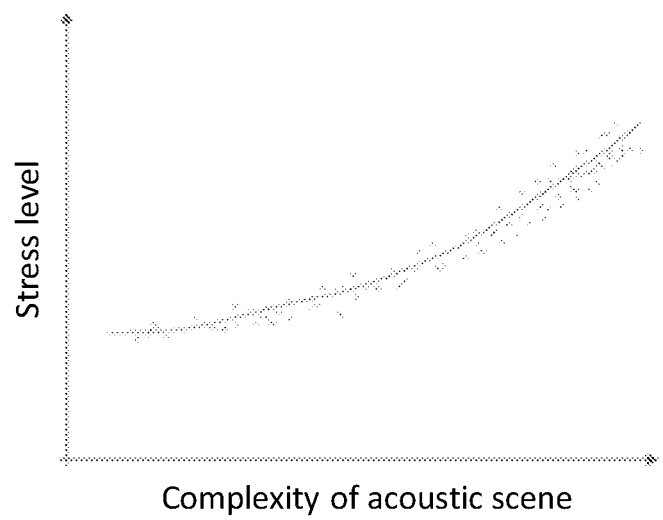
FIG. 7 illustrates dependency of a stress level and a complexity of an acoustic scene, and FIGS. 8a) and 8b) illustrate a detection of an uncompensated hearing loss.

FIG. 7 illustrates dependency of a stress level (y-axis) and a complexity of an acoustic scene (x-axis). From the graph it can be seen that the more complex the acoustic scene is, the stress level will be higher. Such dependency may form part of historical data. The historical data may define expected stress parameter. The expected stress parameter may depend on the complexity of the acoustic scene.

Figure 8A:
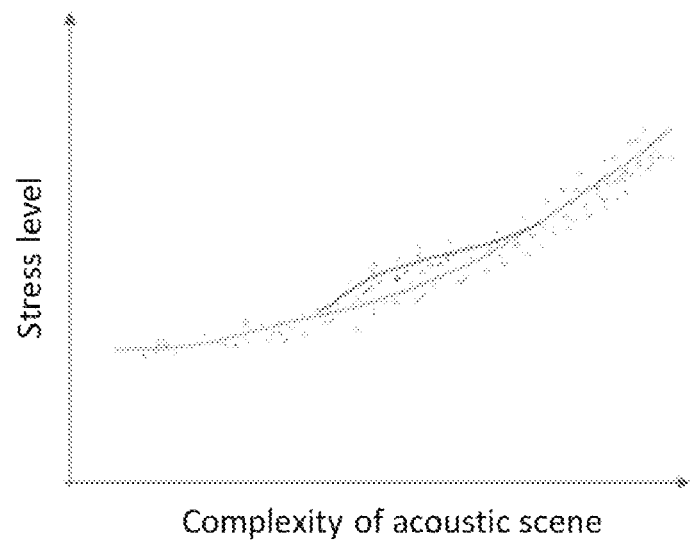
Figure 8B:
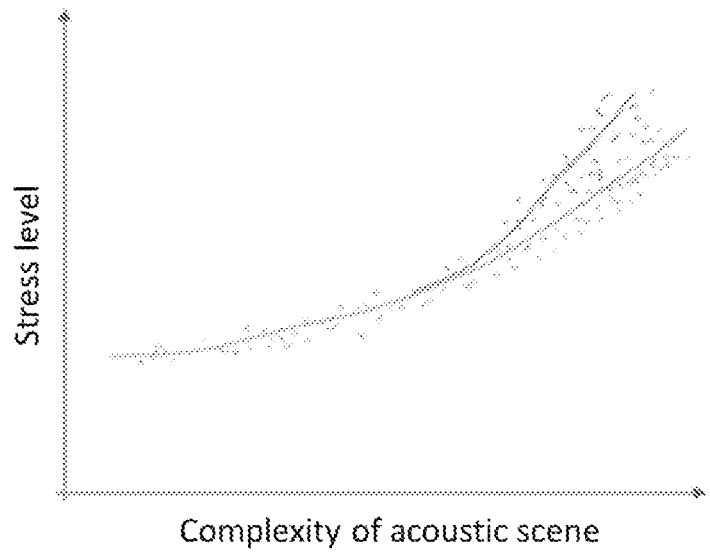

FIGS. 8a) and 8b) illustrate a detection of an uncompensated hearing loss. The graph in FIGS. 8a) and 8b) shows dependency of the stress level (y-axis) on the complexity of an acoustic scene (x-axis). The regular (brighter) curve shows historical data generated over time based on the user's previous experience or based on other users with similar profile. The irregular (darker) curve shows actual stress level measured by at least one stress evaluation device. The irregular (darker) curve shows that the user starts to show higher stress relative to the historical average of acoustic scenes with similar complexity. Such behaviour may be the sign of an uncompensated hearing loss.

Although particular features have been shown and described, it will be understood that they are not intended to limit the claimed invention, and it will be made obvious to those skilled in the art that various changes and modifications may be made without departing from the scope of the claimed invention. The specification and drawings are, accordingly to be regarded in an illustrative rather than restrictive sense. The claimed invention is intended to cover all alternatives, modifications and equivalents.

LIST OF REFERENCES 2 hearing device
4 microphone
6 processing unit
8 speaker
10 wireless communication unit
12 stress evaluation device
14 audio signals
16 processed audio signals
18 stress parameter
20 environment 22 user
24 acoustic scene
26 audio sources
28 audio signals
38 package
100 method executed by the hearing device
101 method step of receiving audio signals
102 method step of processing audio signals
103 method step of measuring stress parameters
104 method step of generating an indication of stress
105 method step of determining whether the user is stressed?
106 method step of changing processing parameters
107 method step of checking stress later
200 system
202 external computing device
204 first communication link
206 indication of stress
208 cloud-computing platform
210 second communication link
212 database
300 computer program
300a voice detection/extraction algorithm
300b speech analyser algorithm
300c indication of stress algorithm

The invention claimed is:

1. A computing device comprising:
one or more memory units; and
one or more processing units;
wherein the computing device is configured to communicate with a hearing device configured to receive sound from an environment, the hearing device comprising one or more sensors;
wherein the one or more sensors are configured to measure a stress parameter related to stress of a user of the hearing device, the stress parameter being related to an acoustic scene;
wherein the computing device is configured to obtain the measured stress parameter;
wherein the one or more processing units of the computing device comprise a program configured to determine an indication of stress of the user based on at least the measured stress parameter;
wherein the computing device is configured to cause a request to change a parameter of the hearing device to be provided to the user, wherein the request is based on the determined indication of stress of the user, and allows the user to have a freedom to decide whether to change the parameter of the hearing device, and wherein the computing device is configured to send the indication of stress of the user to the hearing device.

2. The computing device according to claim 1, wherein the computing device is configured to send the request to the hearing device.

3. The computing device according to claim 1, wherein the program of the computing device is configured to determine the indication of stress based also on a speech of the user.

4. The computing device according to claim 1, wherein the one or more sensors comprise a temperature sensor, a heart rate sensor, a skin resistance sensor, one or more microphones, or any combination of the foregoing.

5. The computing device according to claim 1, wherein the indication of stress comprises the request to change the parameter of the hearing device.

6. The computing device according to claim 1, wherein the computing device is configured to receive speech data from the hearing device, the speech data indicating a speech of the user.

7. The computing device according to claim 1, wherein the computing device comprises a database comprising historical data, the historical data relating to a perceptual hearing of the user and/or a general perceptual hearing, wherein the indication of stress is determined based on the historical data.

8. The computing device according to claim 1, wherein the computing device is configured to receive data comprising acoustic scene information, and determine the indication of stress of the user based on the data.

9. A system comprising the computing device according to claim 1, and the hearing device.

10. The computing device of claim 1, wherein the computing device is configured to determine if a stress of the user is above a stress threshold.

11. The computing device of claim 10, wherein the computing device is configured to cause the request to change the parameter of the hearing device to be provided to the user after the stress of the user is determined to be above the stress threshold.

12. The computing device of claim 1, wherein the request to change the parameter of the hearing device comprises a suggestion to increase a volume, and wherein the suggestion to increase the volume is based on the determined indication of stress of the user.

13. The computing device of claim 1, wherein the request to change the parameter of the hearing device comprises a suggestion to change an operation mode of the hearing device, and wherein the suggestion to change the operation mode of the hearing device is based on the determined indication of stress of the user.

14. The computing device of claim 1, wherein the request to change the parameter of the hearing device comprises a suggestion to change a setting of the hearing device, and wherein the suggestion to change the setting of the hearing device is based on the determined indication of stress of the user.

15. A computing device comprising:
one or more memory units; and
one or more processing units;
wherein the computing device is configured to communicate with a hearing device configured to receive sound from an environment, the hearing device comprising one or more sensors;
wherein the one or more sensors are configured to measure a stress parameter related to stress of a user of the hearing device, the stress parameter being related to an acoustic scene;
wherein the computing device is configured to obtain the measured stress parameter:
wherein the one or more processing units of the computing device comprise a program configured to determine an indication of stress of the user based on at least the measured stress parameter; and
wherein the computing device is configured to detect an uncompensated hearing loss of the user after the indication of stress is determined.

16. The computing device according to claim 15, wherein the program of the computing device is configured to detect the hearing deficit of the user, and/or the uncompensated hearing loss of the user, and/or the change in the hearing capability of the user, based on the indication of stress.

17. A hearing device comprising:
a processing unit;
a speaker; and
a wireless communication unit;
wherein the processing unit is configured to process audio signals to obtain processed audio signals;
wherein the speaker is configured to provide output sound based on the processed audio signals;
wherein the hearing device is configured to change a parameter of the hearing device after receiving a stress indicator, wherein the parameter is different from a volume control, and affects how the processing unit processes the audio signals, and wherein the stress indicator is indicative of a stress of a user of the hearing device; and
wherein the hearing device is configured to decide, based on the stress indicator, whether to change the parameter.

18. The hearing device of claim 17, wherein the hearing device is configured to change the parameter by changing a mode of the hearing device.

19. The hearing device of claim 17, wherein the hearing device is configured to change the parameter by changing a setting of the hearing device.

20. The hearing device of claim 17, wherein the hearing device is configured to change the parameter by increasing a volume.

21. A system comprising:
a hearing device configured to be worn by a user, the hearing device comprising a processing unit, a speaker, and a wireless communication unit, wherein the processing unit is configured to process audio signals to obtain processed audio signals, the speaker being configured to provide output sound based on the processed audio signals to the user; and
one or more sensors configured to be coupled to, or carried by, the user, the one or more sensors configured to measure a stress parameter related to stress of the user, the stress parameter being related to an acoustic scene;
wherein the one or more sensors are configured to output the measured stress parameter for processing by an external computing device;
wherein the hearing device is configured to decide whether to adjust a parameter of the hearing device based on a stress indicator received from the external computing device.

22. The system according to claim 21, wherein the hearing device comprises the one or more sensors.

23. The system according to claim 21, wherein the one or more sensors comprise one or more microphones.

24. The system according to claim 23, wherein the hearing device comprises the one or more microphones.

25. The system according to claim 21, wherein the stress indicator comprises a suggestion from the external computing device.

26. The system according to claim 21, wherein the hearing device comprises one or more microphones configured to provide the audio signals.

27. The system according to claim 21, wherein the one or more sensors comprise a temperature sensor, a heart rate sensor, a skin resistance sensor, one or more microphones, or any combination of the foregoing.

28. The system according to claim 21, wherein the stress indicator comprises a request to adjust the parameter.

29. The system according to claim 21, wherein the hearing device is configured to send speech data indicating at least a part of a speech of the user to the external computing device.

30. The system according to claim 21, further comprising the external computing device.

31. The system of claim 21, wherein the parameter is a mode parameter of the hearing device, and wherein the hearing device is configured to decide whether to adjust the mode parameter of the hearing device based on the stress indicator received from the external computing device.

32. The system of claim 21, wherein the parameter is a processing parameter of the hearing device, and wherein the hearing device is configured to decide whether to adjust the processing parameter of the hearing device based on the stress indicator received from the external computing device.

33. The system of claim 32, wherein the hearing device is configured to adjust the processing parameter by increasing a volume.

34. The system of claim 32, wherein the processing parameter is different from a volume parameter.

35. The system of claim 21, wherein the parameter is a setting parameter of the hearing device, and wherein the hearing device is configured to decide whether to adjust the setting parameter of the hearing device based on the stress indicator received from the external computing device.

* * * * *